United States Patent
Jerussi et al.

(10) Patent No.: US 7,189,715 B2
(45) Date of Patent: Mar. 13, 2007

(54) COMPOSITIONS COMPRISING ZOPICLONE DERIVATIVES AND METHODS OF MAKING AND USING THE SAME

(75) Inventors: Thomas P. Jerussi, Framingham, MA (US); Qun K. Fang, Wellesley, MA (US)

(73) Assignee: Sepracor Inc., Marlborough, MA (US)

( * ) Notice: Subject to any disclaimer, the term of this patent is extended or adjusted under 35 U.S.C. 154(b) by 320 days.

(21) Appl. No.: 10/691,628

(22) Filed: Oct. 24, 2003

(65) Prior Publication Data

US 2004/0147521 A1    Jul. 29, 2004

Related U.S. Application Data

(60) Provisional application No. 60/420,740, filed on Oct. 24, 2002.

(51) Int. Cl.
*A61K 31/5375* (2006.01)
*A61K 31/496* (2006.01)
*C07D 215/30* (2006.01)
*C07D 413/14* (2006.01)

(52) U.S. Cl. .................. 514/234.2; 544/106; 544/111; 544/116; 544/117; 544/224; 544/235; 544/236; 514/231.2; 514/233.5; 514/252.11

(58) Field of Classification Search .............. 544/106, 544/111, 116, 117, 224, 235, 236; 514/231.2, 514/233.5, 234.2, 252.11
See application file for complete search history.

(56) References Cited

U.S. PATENT DOCUMENTS

| | | | | |
|---|---|---|---|---|
| 6,136,327 | A * | 10/2000 | Gupta et al. | 424/400 |
| 6,294,192 | B1 * | 9/2001 | Patel et al. | 424/451 |
| 6,339,086 | B1 * | 1/2002 | Jerussi et al. | 514/249 |
| 6,348,485 | B1 * | 2/2002 | Ohkawa et al. | 514/394 |
| 6,458,791 | B1 * | 10/2002 | Jerussi et al. | 514/249 |
| 6,946,464 | B2 * | 9/2005 | Jerussi et al. | 514/249 |

* cited by examiner

*Primary Examiner*—Golam M. M. Shameem
(74) *Attorney, Agent, or Firm*—Jones Day

(57) ABSTRACT

The invention is directed to racemic and stereomerically pure compounds of Formula 3:

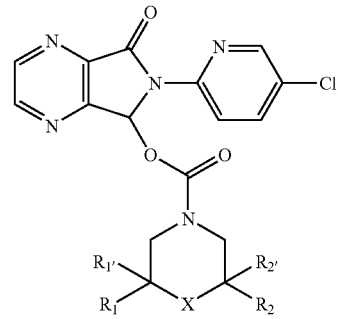

Formula 3 and to pharmaceutical compositions comprising them, methods of their use, and methods of their preparation.

16 Claims, No Drawings

COMPOSITIONS COMPRISING ZOPICLONE DERIVATIVES AND METHODS OF MAKING AND USING THE SAME

This application claims priority to U.S. Provisional Application No. 60/420,740, filed Oct. 24, 2002, the entirety of which is incorporated herein by reference.

1. FIELD OF THE INVENTION

The invention relates to derivatives of zopiclone, pharmaceutical compositions and dosage forms comprising the same, and methods of making and using the same.

2. BACKGROUND OF THE INVENTION

Zopiclone, chemically named (±)-6-(5-chloro-2-pyridinyl)-6,7-dihydro-7-oxo-5H-pyrrolo -[3,4b]pyrazin-5-yl-4-methylpiperazine-1-carboxylate, is a non-benzodiazepine hypnotic which has the following structure:

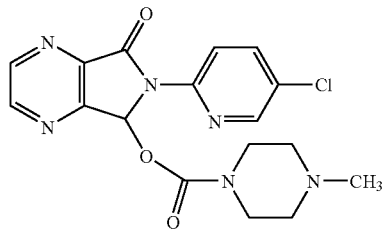

Zopiclone and some of its uses are described by U.S. Pat. Nos. 3,862,149 and 4,220,646. Uses of the optically pure (+) and (−) enantiomers of the drug (i.e., (+) -zopiclone and (−)-zopiclone) are described in U.S. Pat. No. 5,786,357 and WO 93/10788, respectively.

Zopiclone reportedly binds at or near benzodiazepine sites on GABA A macromolecular receptor complexes. Goa, K. L. and Heel, R. C. *Drugs,* 32:48–65 (1986). These complexes are located both within the central nervous system and peripherally (e.g., in the endocrine system), and contain binding sites for benzodiazepines and GABA. Verma, A. and Snyder, S. H., *Annu. Rev. Pharmacol. Toxicol.* 29:307–22 (1989). GABA receptor complexes are further associated with, and interact with, membrane channels for chloride ion transport. Upon binding to a benzodiazepine site, zopiclone is believed to allosterically modulate the activity of the complex by increasing transmembrane conductance of chloride ions. This stabilizes neuronal membrane potentials and dampens excitatory input. See Meldrum, B. S., *Brit. J. Clin. Pharm.* 27(suppl.1): S3–S11 (1989); *Goodman & Gilman's The Pharmacological Basis of Therapeutics,* Hardman, J. G., et al., eds. p. 365 (9th ed., 1996).

The metabolism of zopiclone is rapid, complex, and differs among species. Gaillot, J., et al., *Pharmacology* 27(supp.2): 76–91 (1983). Of the more than ten metabolites of the compound that have been identified, however, only two reportedly exhibit pharmacological activity in humans: N-desmethylzopiclone and zopiclone-N-oxide. See Goa, K. L. and Heel, R. C. *Drugs,* 32:48–65 (1986) ("Goa"); U.S. Pat. No. 6,339,086. Other zopiclone metabolites are reportedly inactive. Goa, FIG. 3, page 59.

Although chemically unrelated to the benzodiazepines, zopiclone exhibits pharmacological activity similar to benzodiazepines. Goa. For example, zopiclone and its optically pure enantiomers are reportedly useful in the treatment of diseases and conditions including, but not limited to, epilepsy, anxiety, aggressive behavior, muscle tension, behavioral disorders, depression, schizophrenia, and endocrine disorders. See, e.g., WO 93/10787. Racemic zopiclone has also been used to improve sleep in adults and geriatric patients with several types of sleep disorders including situational, transient primary and secondary insomnia. See, e.g., Brun, J. P., *Pharm. Biochem. Behav.* 29: 831–832 (1988).

Some compounds which bind to benzodiazepine sites also have an affinity for muscarinic receptors such as acetylcholine receptors. Julou, L., et al., *Pharmacol. Biochem. Behav.* 23:653–659 (1985). Consequently, administration of such compounds can result in adverse effects such as, but are not limited to, drymouth, thirst, slowing and acceleration of the heart, dilated pupils, blurred vision, restlessness, fatigue, headache, hallucinations and delirium. *Goodman & Gilman's The Pharmacological Basis of Therapeutics,* Hardman, J. G., et al., eds. p. 142 (9th ed., 1996). Many of these same adverse effects are exhibited by racemic zopiclone. Particular adverse effects exhibited by the racemic zopiclone include, but are not limited to, the development of a bitter taste due to salivary secretion of the drug, dry mouth, heart palpitations, drowsiness, morning tiredness, headache, dizziness, impairment of psychomotor skills and related effects. Compounds are therefore desired that can be used for the treatment or prevention of various disorders, but which have reduced, fewer, or different adverse effects than racemic zopiclone.

3. SUMMARY OF THE INVENTION

The invention is directed, in part, to racemic and stereomerically pure derivatives of zopiclone and pharmaceutically acceptable prodrugs, salts, solvates, hydrates, and clathrates thereof. Preferred derivatives are stereomerically pure. The invention is also directed to compositions comprising racemic and stereomerically pure derivatives of zopiclone and pharmaceutically acceptable prodrugs, salts, solvates, hydrates, and clathrates thereof. Preferred compositions are pharmaceutical compositions (e.g., single unit dosage forms) suitable for administration to patients (e.g., mammals, preferably humans).

The invention is also directed to methods of treating and preventing a variety of diseases and disorders which comprise the administration to a patient in need of such treatment or prevention of a therapeutically or prophylactically effective amount of a racemic and stereomerically pure derivative of zopiclone. Specific methods of the invention further comprise the administration of a second pharmacologically active compound to the patient.

The invention further encompasses methods of preparing racemic and stereomerically pure derivatives of zopiclone.

3.1 DEFINITIONS

As used herein, and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise —NO, —NO$_2$, —ONO, or —ONO$_2$ moieties. The term "prodrug" is accorded a meaning herein such that prodrugs of zopiclone derivatives do not encompass zopiclone, zopiclone-N-oxide, or N-desmethylzopiclone. When used to describe a compound of the invention, the term "prodrug" may also to be interpreted to exclude other compounds of the invention.

As used herein, and unless otherwise indicated, the terms "biohydrolyzable carbamate," "biohydrolyzable carbonate," "biohydrolyzable ureide" and "biohydrolyzable phosphate" mean a carbamate, carbonate, ureide and phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, and unless otherwise indicated, the term "biohydrolyzable ester" means an ester of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters.

As used herein, and unless otherwise indicated, the term "biohydrolyzable amide" means an amide of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable amides include, but are not limited to, lower alkyl amides, α-amino acid amides, alkoxyacyl amides, and alkylaminoalkylcarbonyl amides.

As used herein, and unless otherwise indicated, the term "alkyl" includes saturated monovalent linear, branched, and cyclic hydrocarbon radicals. An alkyl group can include one or more double or triple bonds. It is understood that cyclic alkyl groups comprise at least three carbon atoms.

As used herein, and unless otherwise indicated, the term "lower alkyl" means branched or linear alkyl having from 1 to 6, more preferably from 1 to 4 carbon atoms. Examples include, but are not limited to, methyl, ethyl, propyl, isopropyl, isobutyl, and tertiary butyl.

As used herein, and unless otherwise indicated, the term "aryl" includes an organic radical derived from an aromatic hydrocarbon by removal of one hydrogen, such as phenyl or naphthyl.

As used herein, and unless otherwise indicated, the term "aralkyl" means an aryl substituted with one or linear, branched, or cyclic alkyl groups. Aralkyl moieties can be attached to other moieties through their aryl or alkyl components.

As used herein, and unless otherwise indicated, the term "substituted" as used to describe a compound or chemical moiety means that at least one hydrogen atom of that compound or chemical moiety is replace with a second chemical moiety. Examples of second chemical moieties include, but are not limited to: halogen atoms (e.g., chlorine, bromine, and iodine); $C_1$–$C_6$ linear, branched, or cyclic alkyl (e.g., methyl, ethyl, butyl, and tert-butyl); hydroxyl; thiols; carboxylic acids; and primary, secondary or tertiary amines (e.g., —$NH_2$, —$NH(CH_3)$, —$N(CH_3)_2$, and cyclic amines). Preferred second chemical moieties are chlorine, hydroxyl, amine, thiol, and carboxylic acid.

As used herein, and unless otherwise indicated, a composition that is "substantially free" of a compound means that the composition contains less than about 20% by weight, more preferably less than about 10% by weight, even more preferably less than about 5% by weight, and most preferably less than about 3% by weight of the compound.

As used herein, and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein, and unless otherwise indicated, the term "enantiomerically pure" means a stereomerically pure composition of a compound having one chiral center.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

As used herein, the term "pharmaceutically acceptable salt" refers to salts prepared from pharmaceutically acceptable non-toxic acids, including inorganic acids and organic acids. Suitable non-toxic acids include inorganic and organic acids such as, but not limited to, acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isethionic, lactic, maleic, malic, mandelic, methanesulfonic, mucic, nitric, pamoic, pantothenic, phenylacetic, propionic, phosphoric, salicylic, stearic, succinic, sulfanilic, sulfuric, tartaric acid, p-toluenesulfonic and the like. Particularly preferred are hydrochloric, hydrobromic, phosphoric, and sulfuric acids, and most particularly preferred is the hydrochloride salt.

As used herein, the term "hydrate" means a compound of the present invention or a salt thereof, that further includes a stoichiometric or non-stoichiometric amount of water bound by non-covalent intermolecular forces.

As used herein, the term "clathrate" means a compound of the present invention or a salt thereof in the form of a crystal lattice that contains spaces (e.g., channels) that have a guest molecule (e.g., a solvent or water) trapped within.

As used herein, and unless otherwise specified, the terms "treat," "treating" and "treatment" refer to the eradication or amelioration of the disease or one or more symptoms associated with the disease. In certain embodiments, the terms refer to minimizing the spread or worsening of the disease resulting from the administration of one or more prophylactic or therapeutic agents to a subject with such a disease.

As used herein, and unless otherwise specified, the terms "prevent," "preventing" and "prevention" refer to the prevention of the onset, recurrence or spread of the disease or a symptom thereof.

As used herein, and unless otherwise specified, a "therapeutically effective amount" of a compound is an amount sufficient to provide a therapeutic benefit in the treatment or management of the disease or to delay or minimize one or more symptoms associated with the disease. Further, a therapeutically effective amount of a compound means that amount of therapeutic agent alone, or in combination with other therapies, provides a therapeutic benefit in the treatment or management of the disease. The term "therapeutically effective amount" can encompass an amount that improves overall therapy, reduces or avoids symptoms or causes of disease, or enhances the therapeutic efficacy of another therapeutic agent.

As used herein, and unless otherwise specified, a "prophylactically effective amount" of a compound is an amount sufficient to result in the prevention, recurrence or spread of the disease. A prophylactically effective amount may refer to an amount sufficient to prevent initial disease, the recurrence or spread of the disease or the occurrence of the disease in a patient including, but not limited to, those predisposed to the disease. A prophylactically effective amount may also refer to an amount that provides a prophylactic benefit in the prevention of the disease. Further, a prophylactically effective amount of a compound means that amount alone, or in combination with other agents, provides a prophylactic benefit in the prevention of the disease. The term "prophylactically effective amount" can encompass an amount that improves overall prophylaxis or enhances the prophylactic efficacy of another prophylactic agent.

4. DETAILED DESCRIPTION OF THE INVENTION

This invention relates, in part, to racemic and stereomerically pure compounds of Formula 1:

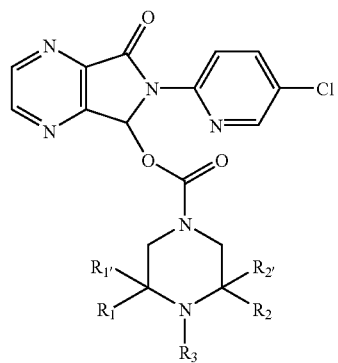

Formula 1 and pharmaceutically acceptable salts, solvates, hydrates, prodrugs, and clathrates thereof, wherein $R_1$ and $R_{1'}$ are both H or when taken together are =O, $R_2$ and $R_{2'}$ are both H or when taken together are =O, and $R_3$ is H, alkyl, aryl, arylalkyl or —$COR_4$; wherein $R_4$ is H, amine (e.g., N(alkyl)(alkyl), N(lower alkyl)(alkyl), N(H)(alkyl), N(H)(lower alkyl), and $NH_2$), alkyl, alkoxy, aryl, aryloxy, arylalkyl, or O-arylalkyl; provided that when $R_1$, $R_{1'}$, $R_2$, and $R_{2'}$ are all H, $R_3$ is not H or methyl. Preferred compounds of Formula 1 are stereomerically pure.

In specific compounds of Formula 1, $R_1$, $R_{1'}$, $R_2$, and $R_{2'}$ are all H and $R_3$ is —$COR_4$, wherein $R_4$ is H, alkyl (e.g., lower alkyl), $NH_2$ or alkoxyalkyl. In more specific compounds, $R_4$ is H, $CH_3$, $NH_2$ or —$OCH_2CH_3$.

In other specific compounds, $R_1$ and $R_{1'}$ are both H. In still other specific compounds, $R_1$ and $R_{1'}$ are taken together to form =O, $R_2$ and $R_{2'}$ are both H, and $R_3$ is H or alkyl (e.g., lower alkyl, such as methyl).

Examples of compounds of Formula 1 are shown below:

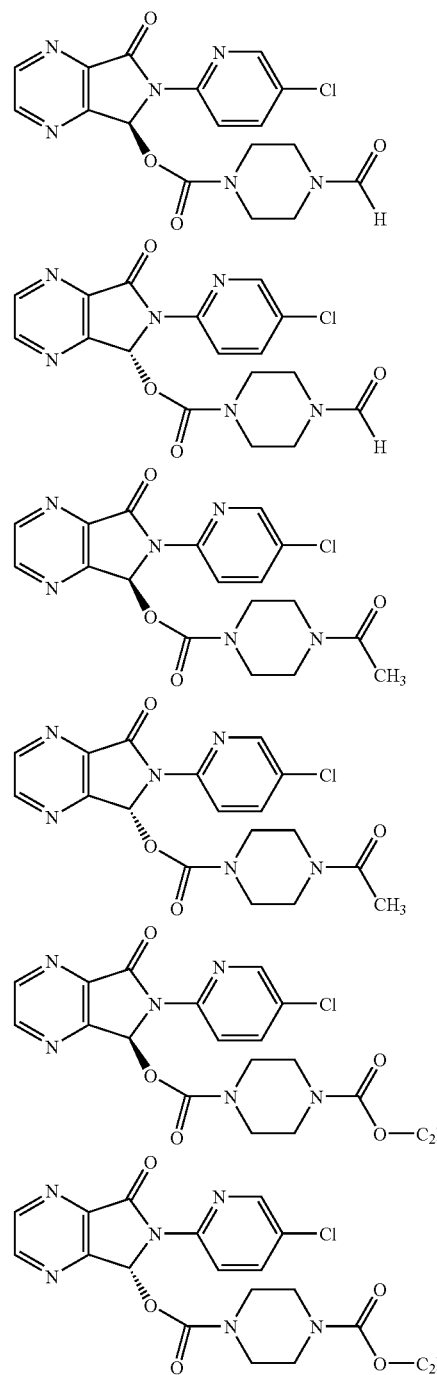

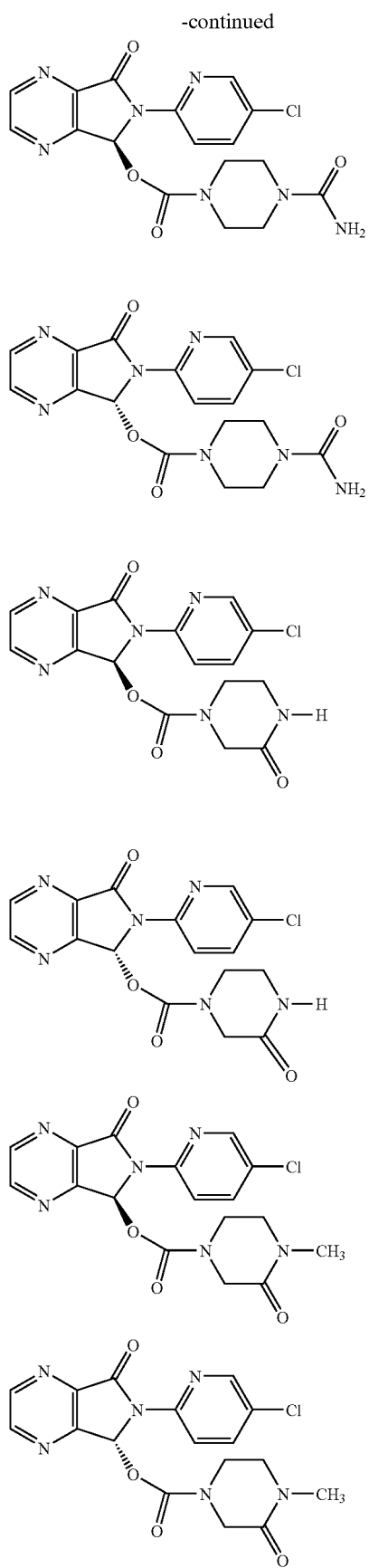
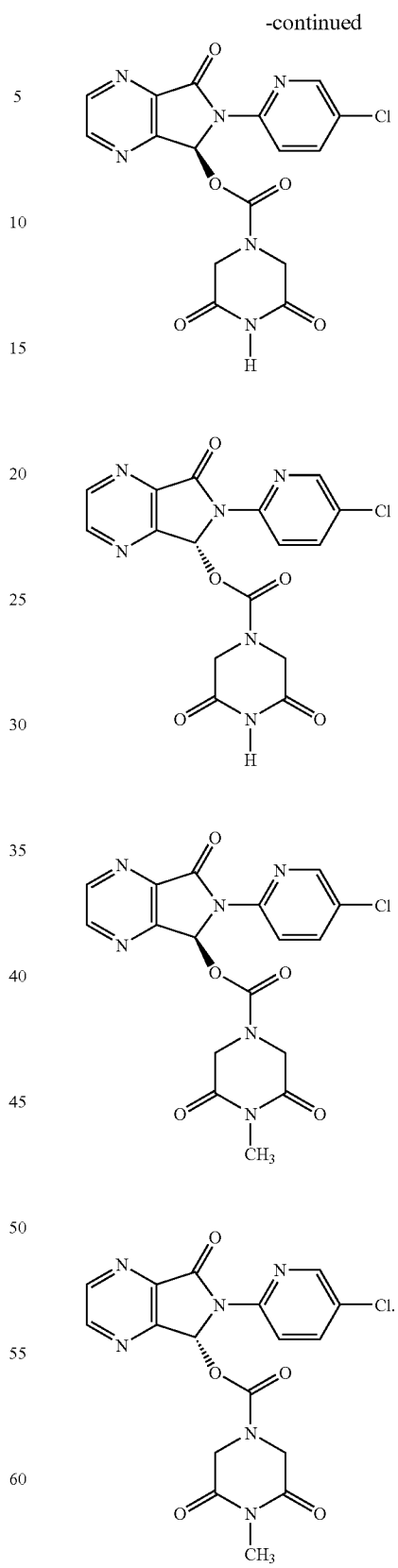
This invention also encompasses racemic and stereomerically pure compounds of Formula 2:

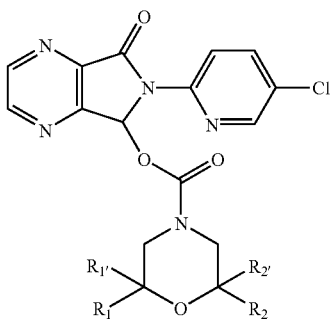

Formula 2 and pharmaceutically acceptable salts, solvates, hydrates, prodrugs, and clathrates thereof, wherein $R_1$ and $R_{1'}$ are both H or when taken together are =O; and $R_2$ and $R_{2'}$ are both H or when taken together are =O. Preferred compounds of Formula 2 are stereomerically pure. In a specific embodiment, $R_1$, $R_{1'}$, $R_2$ and $R_{2'}$ are all H.

Compounds of Formulas 1 and 2 are referred to herein as "zopiclone derivatives." The invention encompasses mixtures of two or more racemic and stereomerically pure zopiclone derivatives. For example, it encompasses non-racemic mixtures of stereoisomers of the same compound (e.g., about 90, 80, 70, or 60 weight percent of one enantiomer and about 10, 20, 30, or 40 weight percent of the opposite enantiomer); and mixtures of different racemic or stereomerically pure compounds (e.g., about 90, 80, 70, or 60 weight percent of one compound and about 10, 20, 30, or 40 weight percent of another).

The invention further relates to pharmaceutical compositions comprising zopiclone derivatives or mixtures, pharmaceutically acceptable salts, solvates, hydrates, prodrugs, or clathrates thereof, as well as to methods of treating or preventing diseases or conditions using them. The invention also encompasses methods of synthesizing and purifying zopiclone derivatives.

A first embodiment of the invention encompasses zopiclone derivatives and pharmaceutically acceptable salts, solvates, hydrates, prodrugs, and clathrates thereof. Preferred compounds are stereomerically pure.

Another embodiment of the invention encompasses a pharmaceutical composition comprising a zopiclone derivative, or a pharmaceutically acceptable salt, solvate, hydrate, prodrug, or clathrate thereof. In a specific composition, the zopiclone derivative is stereomerically pure. Pharmaceutical compositions of the invention include single unit dosage forms, which may be suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Preferred single unit dosage forms are tablets, capsules and caplets.

Another embodiment of the invention encompasses a method of treating or preventing a disease or condition which is affected by the modulation of one or more central benzodiazepine sites in a patient which comprises administering to a patient in need of such treatment or prevention a therapeutically or prophylactically effective amount of a zopiclone derivative, or a pharmaceutically acceptable salt, solvate, hydrate, prodrug, or clathrate thereof. In a specific method, the zopiclone derivative is stereomerically pure.

As used herein, the terms "diseases and conditions which are affected by the modulation of one or more central benzodiazepine sites," "diseases and conditions which are affected by the modulation of one or more benzodiazepine sites," and "disease or condition affected by the modulation of a benzodiazepine site" mean a disease or condition that has at least one symptom which is mitigated or alleviated by allosteric binding of a compound to benzodiazepine sites. Typically, at least one symptom is mitigated or alleviated by an increase in the transneuronal membrane chloride current associated with the binding of only GABA to benzodiazepine receptor complexes. Specific diseases and conditions that are affected by the modulation of one or more benzodiazepine receptors include, but are not limited to: anxiety; affective disorders such as depression, attention deficit disorder ("ADD"), and attention deficit disorder with hyperactivity ("ADDH") or attention deficit/hyperactivity disorder ("ADHD"); convulsive disorders such as epilepsy; aggressive behavior; spasticity or acute muscle spasm; behavioral disorders such as mood anxiety and schizophrenia; and alcohol and drug addiction.

Another embodiment of the invention encompasses a method of treating or preventing anxiety in a patient which comprises administering to a patient in need of such treatment or prevention a therapeutically or prophylactically effective amount of a zopiclone derivative, or a pharmaceutically acceptable salt, solvate, hydrate, prodrug, or clathrate thereof. In a specific method, the zopiclone derivative is stereomerically pure. The anxiety may be acute or chronic anxiety, or may be a general anxiety disorder.

As used herein, the phrases "treating or preventing anxiety" and "treatment and prevention of anxiety" mean reducing the severity of at least one symptom associated with acute anxiety, chronic anxiety, general anxiety disorder caused by psychologic and/or physiologic factors, and other anxiety disorders such as panic disorders, mood anxiety, panic attacks, phobias, obsessive-compulsive disorders, or post traumatic distress disorder. Symptoms associated with acute anxiety include, but are not limited to, a fear of losing control of one's own actions, a sense of terror arising from no apparent reason, and a dread of catastrophe. Symptoms associated with chronic anxiety include, but are not limited to, uneasiness, nervousness, nagging uncertainty about future events, headache, fatigue, and subacute autonomic symptoms.

Another embodiment of the invention encompasses a method of treating or preventing a convulsive state in a patient which comprises administering to a patient in need of such treatment or prevention a therapeutically or prophylactically effective amount of a zopiclone derivative, or a pharmaceutically acceptable salt, solvate, hydrate, prodrug, or clathrate thereof. In a specific method, the zopiclone derivative is stereomerically pure. A particular method of this embodiment is the treatment or prevention of epilepsy or epileptic seizures.

As used herein, the phrase "treating or preventing a convulsive state" means reducing the severity and/or frequency of at least one symptom associated with convulsive states which include, but are not limited to, recurrent, sudden, and often brief alterations of consciousness, motor activity, sensory phenomena, and autonomic responses which are often characterized by convulsive seizures and/or tonic or clonic jerking of the extremities. The term "convulsive state" encompasses epilepsy and specific types of epileptic seizures including, but not limited to, Tonic-clonic (Grand Mal), Partial (Focal) seizures, psychomotor (Complex partial) seizures, pyknoepileptic or Absence (Petit Mal) seizure, and Myoclonic seizures.

Another embodiment of the invention encompasses a method of treating or preventing an affective disorder in a patient which comprises administering to a patient in need of such treatment or prevention a therapeutically or prophylactically effective amount of a zopiclone derivative, or a pharmaceutically acceptable salt, solvate, hydrate, prodrug, or clathrate thereof. In a specific method, the zopiclone derivative is stereomerically pure. A particular method encompassed by this embodiment is the treatment or prevention of depression. Another method encompassed by this embodiment is the treatment or prevention of attention deficit disorder or attention deficit disorder with hyperactivity.

As used herein, the phrase "treating or preventing an affective disorder" means reducing the severity of at least one symptom associated with a psychological disorder characterized by abnormality of emotional state, including but not limited to, depression, dysthymia, attention deficit disorder, attention deficit disorder with hyperactivity, bipolar disorders, bipolar and manic conditions, and the like. The terms "attention deficit disorder" ("ADD") and "attention deficit disorder with hyperactivity" ("ADDH"), or "attention deficit/hyperactivity disorder" ("ADHD"), are used herein in accordance with the accepted meanings as found in the *Diagnostic and Statistical Manual of Mental Disorders*, 4$^{th}$ Ed., American Psychiatric Association (1997) (DSM-IV™).

As used herein, the phrase "treating or preventing depression" means reducing the severity of at least one symptom associated with depression which include, but are not limited to, changes in mood, feelings of intense sadness, despair, mental slowing, loss of concentration, pessimistic worry, agitation, and self-deprecation. Symptoms associated with depression may also be physical symptoms, which include, but are not limited to, insomnia, anorexia, weight loss, decreased energy and libido, and abnormal hormonal circadian rhythms.

Another embodiment of the invention encompasses a method of treating or preventing aggressive behavior in a patient which comprises administering to a patient in need of such treatment or prevention a therapeutically or prophylactically effective amount of a zopiclone derivative, or a pharmaceutically acceptable salt, solvate, hydrate, prodrug, or clathrate thereof. In a specific method, the zopiclone derivative is stereomerically pure.

As used herein, the phrase "treating or preventing aggressive behavior" means reducing the frequency and/or severity of at least one manifestation of aggressive behavior which include, but are not limited to, aggressive or socially inappropriate vocal outbursts and acts of physical violence.

Another embodiment of the invention encompasses a method of treating or preventing spasticity or acute muscle spasm spasticity in a patient which comprises administering to a patient in need of such treatment or prevention a therapeutically or prophylactically effective amount of a zopiclone derivative, or a pharmaceutically acceptable salt, solvate, hydrate, prodrug, or clathrate thereof. In a specific method, the zopiclone derivative is stereomerically pure.

As used herein, the phrases "treating or preventing spasticity," "treatment and prevention of spasticity," "treating or preventing spasticity and acute muscle spasm," and "treatment and prevention of spasticity and acute muscle spasm" include reducing the severity of at least one symptom associated with a range of abnormalities of skeletal muscle regulation that result from problems of the nervous system. A predominant symptom is heightened muscle tone or hyper-excitability of tonic stretch muscle reflexes. Symptoms of acute muscle spasm include, but are not limited to, trauma, inflammation, anxiety, and pain.

Another embodiment of the invention encompasses a method of treating or preventing a behavioral disorder in a patient which comprises administering to a patient in need of such treatment or prevention a therapeutically or prophylactically effective amount of a zopiclone derivative, or a pharmaceutically acceptable salt, solvate, hydrate, prodrug, or clathrate thereof. In a specific composition, the zopiclone derivative is stereomerically pure.

As used herein, the phrase "treating or preventing a behavioral disorder" means reducing or relieving from at least one symptom of a behavioral disorder, which include, but are not limited to, a subjective sense of terror, a dread of catastrophe, uneasiness, nervousness, uncertainty, headache, fatigue, disturbed thinking, inappropriate effect, auditory hallucinations, and aggressive outbursts.

Another embodiment of the invention encompasses a method of treating or preventing a schizophrenic disorder in a patient which comprises administering to a patient in need of such treatment or prevention a therapeutically or prophylactically effective amount of a zopiclone derivative, or a pharmaceutically acceptable salt, solvate, hydrate, prodrug, or clathrate thereof. In a specific method, the zopiclone derivative is stereomerically pure.

As used herein, the phrase "treating or preventing a schizophrenic disorder" means reducing the severity of at least one symptom associated with schizophrenic disorders. Symptoms of schizophrenic disorders include, but are not limited to, psychotic symptoms of disturbed thinking, feeling and general behavior. Specific symptoms of schizophrenic disorders include the inability to form clear, goal-directed thought, and emotional changes such as blunting and inappropriate affect. Other symptoms of schizophrenic disorders include auditory hallucinations, delusions of persecution, threats of violence, minor aggressive outbursts, aggressive behavior, disturbances of movement such as significant overactivity and excitement, and retardation and stupor.

Another embodiment of the invention encompasses a method of treating alcohol or drug addiction in a patient which comprises administering to a patient in need of such treatment a therapeutically or prophylactically effective amount of a zopiclone derivative, or a pharmaceutically acceptable salt, solvate, hydrate, prodrug, or clathrate thereof. In a specific method, the zopiclone derivative is stereomerically pure.

As used herein, the phrase "treating alcohol or drug addiction" means reducing at least one symptom of disease or conditions related to alcohol or drug addiction including, but not limited to, drug or alcohol addiction or symptoms of withdrawal from alcohol or drugs. Symptoms of withdrawal include, but are not limited to, depression, pain, fever, restlessness, lacrimation, rhinorrhea, uncontrollable yawning, perspiration, piloerection, restless sleep, mydriasis, twitching and muscle spasms, severe aches in the back, abdomen and legs, abdominal and muscle cramps, hot and cold flashes, insomnia, nausea, vomiting, diarrhea, coryza and severe sneezing, and increases in body temperature, blood pressure, respiratory rate, and heart rate.

Another embodiment of the invention encompasses a method of treating or preventing drug withdrawal, alcohol withdrawal, symptoms of drug withdrawal, or symptoms of alcohol withdrawal in a patient which comprises administering to a patient in need of such treatment a therapeutically or prophylactically effective amount of a zopiclone derivative, or a pharmaceutically acceptable salt, solvate, hydrate, prodrug, or clathrate thereof. In a specific method, the zopiclone derivative is stereomerically pure.

Still another embodiment of the invention encompasses methods of preparing zopiclone derivatives, including stereomerically pure enantiomers of those compounds. For example, one method of preparing a compound of Formula 1 comprises contacting a stereomerically pure enantiomer of zopiclone with 1-chloroethyl chloroformate. Another method comprises contacting a stereomerically pure enantiomer of zopiclone with an azodicarboxylate, and hydrolyzing the resulting product under mild conditions. A preferred azodicarboxylate is diethyl azodicarboxylate. Yet another method comprises resolution of a racemic zopiclone derivative using L-N-benzyloxycarbonyl phenylalanine (L-ZPA) as a resolution reagent.

4.1 Synthesis and Isolation of Zopiclone Derivatives

Compounds of this invention (i.e., zopiclone derivatives and pharmaceutically acceptable salts, solvates, hydrates, prodrugs, and clathrates thereof) can be readily prepared from racemic or enantiomerically pure zopiclone. Zopiclone itself can be prepared according to the method disclosed by U.S. Pat. Nos. 3,862,149 and 4,220,646, both of which are incorporated herein by reference. Isolation of enantiomerically pure zopiclone can be achieved using methods well known in the art, such as, but not limited to, chiral chromatography and chiral salt formation. Compounds of the invention can also be prepared by conventional means from racemic or enantiomerically pure N-desmethylzopiclone ("DMZ"), which can be prepared by methods disclosed in U.S. Pat. No. 6,339,086, the entirety of which is incorporated herein by reference.

An exemplary way of preparing a variety of compounds encompassed by this invention is illustrated below in Scheme I:

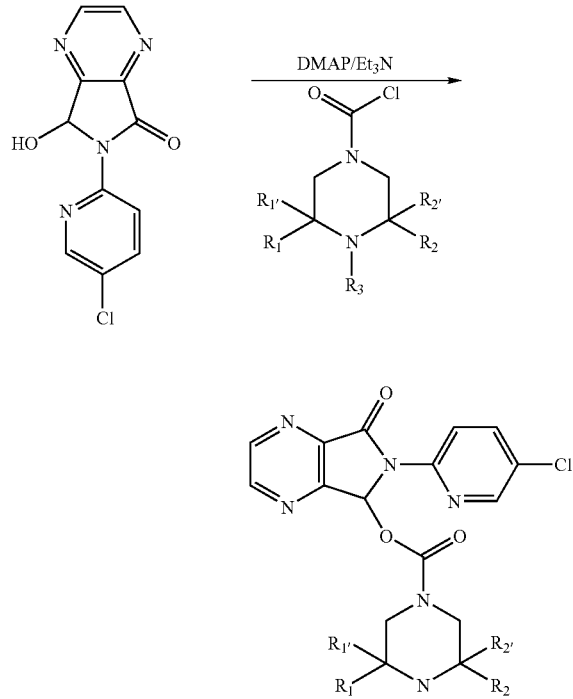

wherein: $R_1$, $R_{1'}$, $R_2$, and $R_{2'}$ are all H and $R_3$ is alkylCO, formyl, or $NH_2CO$; $R_1$ and $R_{1'}$ together are =O, $R_2$, and $R_{2'}$ are both H, and $R_3$ is H or alkyl; or $R_1$ and $R_{1'}$ together are =O, $R_2$ and $R_{2'}$ together are =O, and $R_3$ is H or alkyl. According to this method, the readily available lactomol is treated with the protected piperazine carbamyl chloride in the presence of DMAP and triethylamine. The resulting products can be purified using various methods known in the art, such as column chromatography (silica gel). Well known methods such as chiral chromatography and chiral salt formation can be used to separate stereoisomers of the product. The carbamyl chlorides are prepared from the corresponding piperizine derivative with phosgene in a solvent such as, but not limited to, toluene.

An alternative method of preparing compounds of the invention is illustrated below in Scheme II:

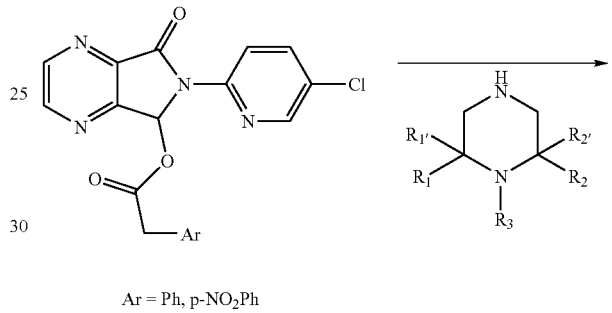

Ar = Ph, p-NO₂Ph

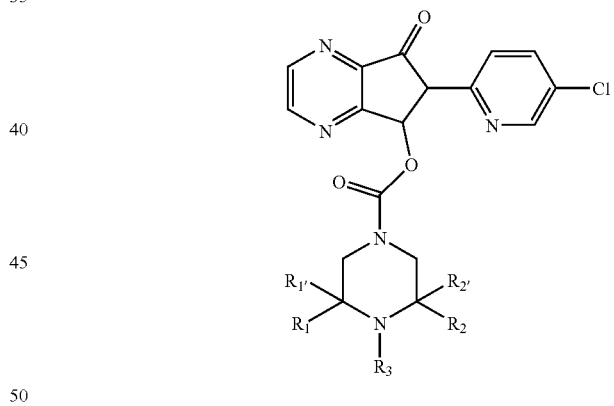

wherein: $R_1$, $R_{1'}$, $R_2$, and $R_{2'}$ are all H and $R_3$ is alkylCO, formyl, or $NH_2CO$; $R_1$ and $R_{1'}$ together are =O, $R_2$, and $R_{2'}$ are both H, and $R_3$ is H or alkyl; or $R_1$ and $R_{1'}$ together are =O, $R_2$ and $R_{2'}$ together are =O, and $R_3$ is H or alkyl. According to this method, the readily available carbonate is reacted with a piperizine derivative in acetonitrile to give the corresponding product. The resulting products can be purified using various methods known in the art, such as column chromatography (silica gel). Well known methods such as chiral chromatography and chiral salt formation can be used to separate stereoisomers of the product.

Compounds of the invention can also be synthesized by a method illustrated below in Scheme III:

Scheme III

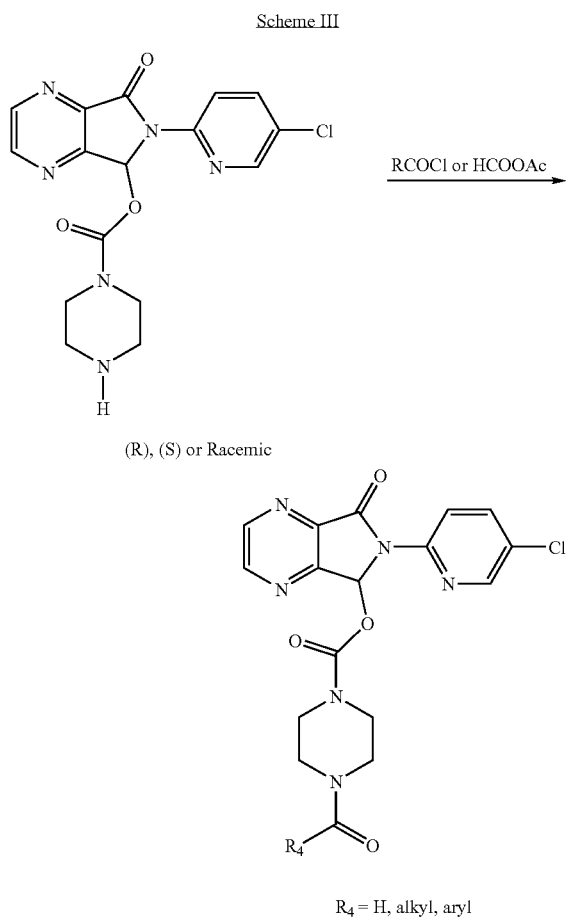

(R), (S) or Racemic $R_4 = H$, alkyl, aryl wherein $R_4$ is H, aryl, or alkyl. According to this method, racemic or enantiomerically pure DMZ is treated with acid chlorides or formic and acetic mixed anhydride to yield the corresponding products. The resulting products can be purified using various methods known in the art, such as column chromatography (silica gel). Well known methods such as chiral chromatography and chiral salt formation can be used to separate and/or further purify stereoisomers of the product.

4.2 Methods of Treatment and Prevention

The magnitude of a prophylactic or therapeutic dose of an active ingredient of the invention in the acute or chronic management of a disease or condition will vary with the nature and severity of the disease or condition, and may also vary according to the route by which the active ingredient is administered.

The dose, and perhaps the dose frequency, will also vary according to the age, body weight, and response of the individual patient. Suitable dosing regimens can be readily selected by those skilled in the art with due consideration of such factors. In general, the recommended daily dose range for the diseases and conditions described herein lie within the range of from about 0.1 mg to about 500 mg per day, given as a single once-a-day dose, or as divided doses from 2 to 4 times throughout the day. Preferably, a daily dose range should be from about 0.5 mg to about 250 mg per day, more preferably, from about 1 mg to about 200 mg per day. In managing the patient, the therapy should be initiated at a lower dose, perhaps about 0.1 mg to about 25 mg, and increased if necessary up to about 1 mg to about 200 mg per day as either a single dose or divided doses, depending on the patient's global response.

It may be necessary to use dosages of the active ingredient outside the ranges disclosed herein in some cases, as will be apparent to those of ordinary skill in the art. Because elimination of zopiclone metabolites from the bloodstream is dependant on renal and liver function, it is recommended that the total daily dose be reduced by at least about 50% in patients with moderate hepatic impairment, and that it be reduced by about 25% in patients with mild to moderate renal impairment. For patients undergoing hemodialysis, it is recommended that the total daily dose be reduced by about 5% and that the dose be withheld until the dialysis treatment is completed. Furthermore, it is noted that the clinician or treating physician will know how and when to interrupt, adjust, or terminate therapy in conjunction with individual patient response.

The phrases "therapeutically effective amount," "prophylactically effective amount," and "therapeutically or prophylactically effective amount" as used herein with respect to the treatment or prevention of diseases and conditions encompasses the above described dosage amounts and dose frequency schedules. Different therapeutically effective amounts may be applicable for different diseases and conditions, as will be readily known by those of ordinary skill in the art. Similarly, amounts sufficient to treat or prevent such disorders, but insufficient to cause adverse effects associated with zopiclone, are also encompassed by the above described dosage amounts and dose frequency schedules.

Any suitable route of administration may be employed for providing the patient with an effective dosage of a compound of the invention. Suitable routes include, but are not limited to, oral, mucosal (e.g., nasal, sublingual, vaginal, buccal, or rectal), parenteral (e.g., subcutaneous, intravenous, bolus injection, intramuscular, or intraarterial), and transdermal.

4.3 Pharmaceutical Compositions and Dosage Forms

Pharmaceutical compositions and dosage forms of the invention comprise one or more of the active ingredients disclosed herein. Pharmaceutical compositions and dosage forms of the invention typically also comprise one or more pharmaceutically acceptable excipients or diluents.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disorder may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients can be accelerated by some excipients such as lactose, or when exposed to water. Active ingredients that comprise primary or secondary amines (e.g., Urea-DMZ and Amido-DMZ) are particularly susceptible to such accelerated decomposition. Consequently, this invention encompasses pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions of the invention can comprise excipients that are well known in the art and are listed, for example, in the U.S. Pharmocopia (USP)SP (XXI)/NF (XVI). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379–80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise a compound of Formula 1 or 2, or a pharmaceutically acceptable salt, solvate, hydrate, or clathrate thereof in an amount of from about 0.1 mg to about 500 mg, preferably in amount of from about 0.5 mg to about 250 mg, and more preferably in an amount of from about 1 mg and about 200 mg.

4.3.1 Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences*, 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Specific oral dosage forms of the invention are coated to avoid the bitter taste associated with zopiclone.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

4.3.2 Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.3.3 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

4.3.4 Transdermal, Topical, and Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences,* 16th and 18th eds., Mack Publishing, Easton Pa. (1980 & 1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

5. EXAMPLES

Certain embodiments of the invention, as well as certain novel and unexpected advantages of the invention, are illustrated by the following non-limiting examples.

5.1 Synthesis of Zopiclone Derivatives

One of the compounds encompassed by this invention, which is referred to herein as "Formyldesmethylzopiclone," "Formyl-DMZ," or "FDMZ," has the following structure:

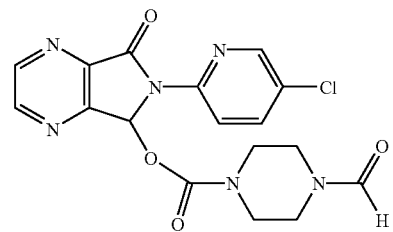

Racemic FDMZ is readily prepared from N-desmethylzopiclone using an appropriate N-dealkylation reaction, while stereomerically pure FDMZ can be prepared from the corresponding enantiomer of N-desmethylzopiclone, as shown below in Scheme IV:

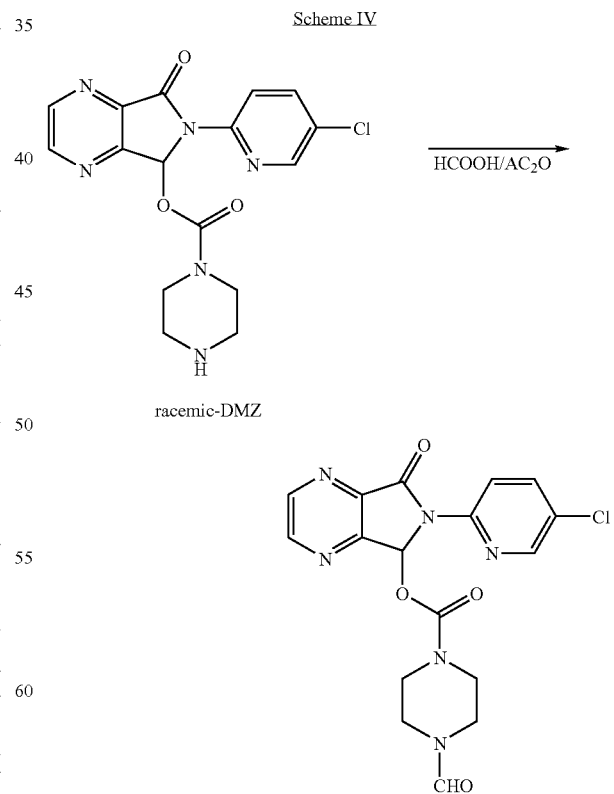

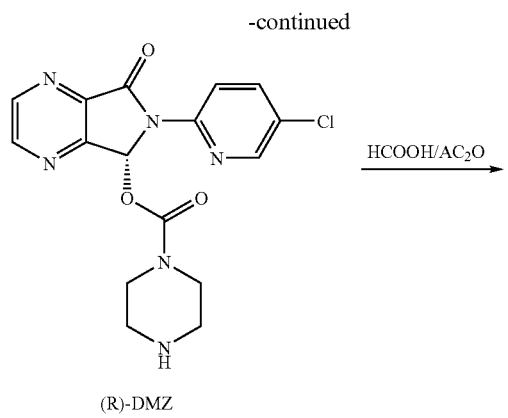

(R)-DMZ

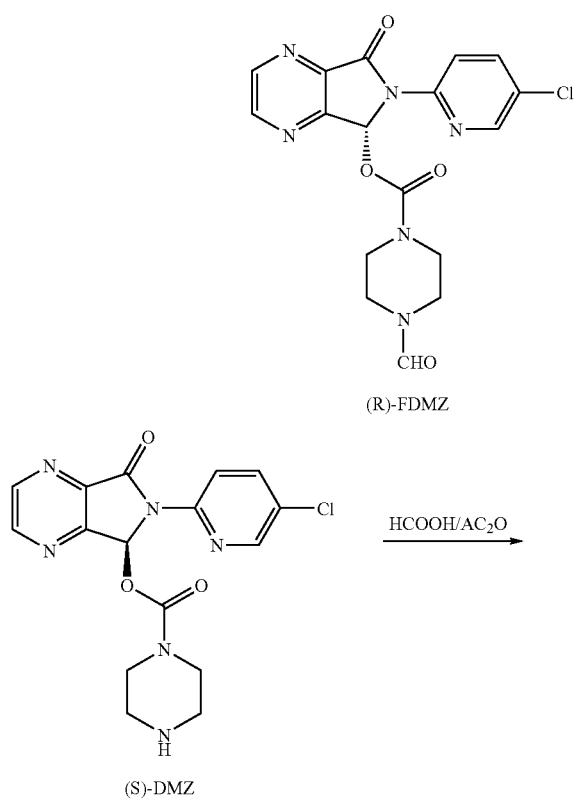

(R)-FDMZ (S)-DMZ (S)-FDMZ

Another compound, which is referred to herein as "Acetyldesmethylzopiclone," "Acetyl-DMZ," or "AcDMZ," and which has the following structure:

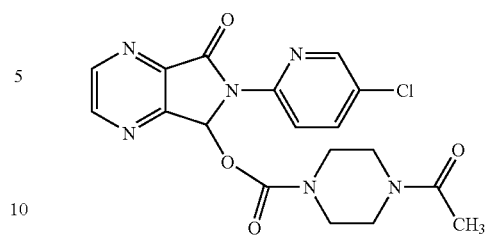

can be prepared in much the same way. In particular, racemic and enantiomerically pure AcDMZ can be synthesized according to the method illustrated above in Scheme IV using acetic acid in place of formic acid.

AcDMZ can also be prepared by treating racemic and enantiomerically pure N-desmethylzopiclone with acylchloride and pyridine. The compound can further be prepared as shown below in Scheme V:

Scheme V

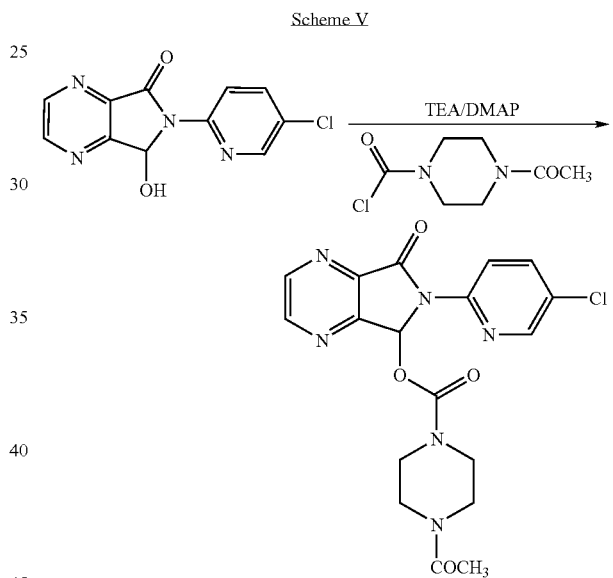

Another compound that can be prepared using methods of the invention is referred to herein as "Carboethoxydesmethylzopiclone," "Carboethoxy-DMZ," or "CDMZ," and has the following structure:

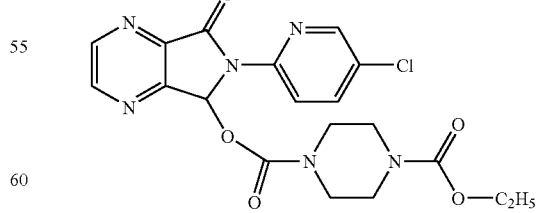

Racemic and enantiomerically pure CDMZ can be synthesized according to the method illustrated in Scheme IV using carboethoxy acetic acid in place of formic acid. Racemic and enantiomerically pure CDMZ can also be prepared by treating racemic and enantiomerically pure N-desmethylzopiclone with ethyl chloroformate. Another method of preparing CDMZ is illustrated below in Scheme VI:

Scheme VI

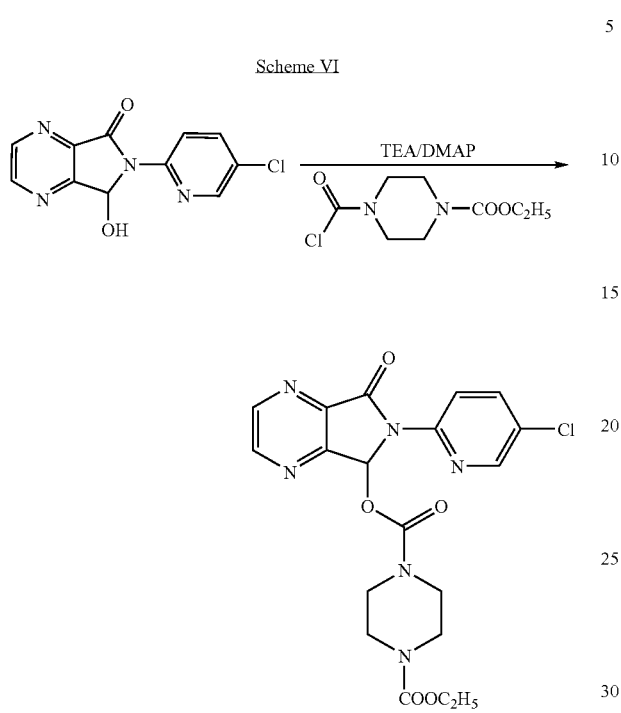

Still another compound of the invention is referred to herein as "Ureadesmethylzopiclone," "Urea-DMZ," or "UDMZ," and has the following structure:

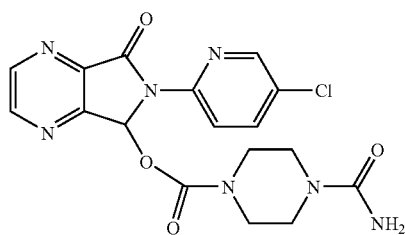

UDMZ can be prepared as illustrated below in Scheme VII:

Scheme VII

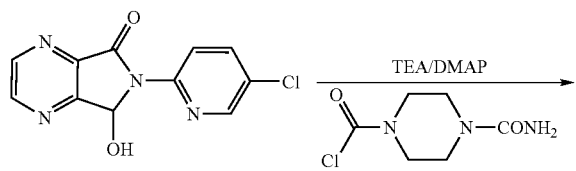

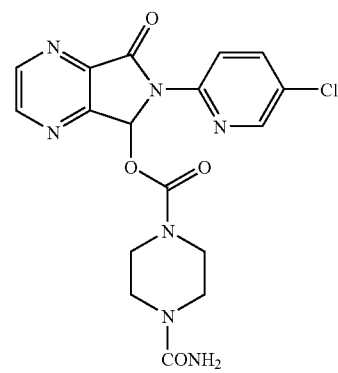

Enantiomerically pure UDMZ can be isolated using known techniques, such as chiral chromatography.

Another compound of this invention, which is referred to herein as "Amidodesmethylzopiclone," "Amido-DMZ," or "AmDMZ," has the following structure:

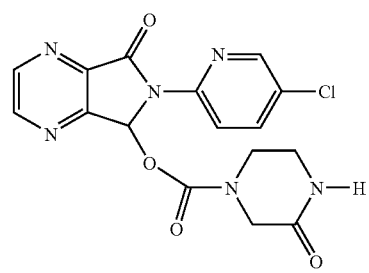

Still another compound, which is referred to herein as "Methylamidodesmethylzopiclone," "Methyladmido-DMZ," or "MAmDMZ," has the following structure:

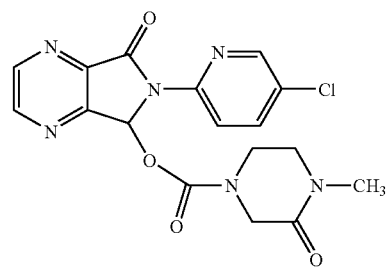

A preferred method of preparing compounds such as AmDMZ and MAmDMZ is illustrated below in Scheme VIII:

Scheme VIII

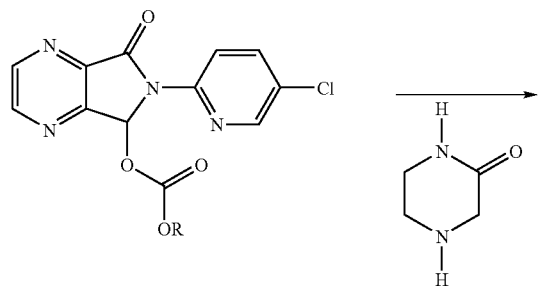

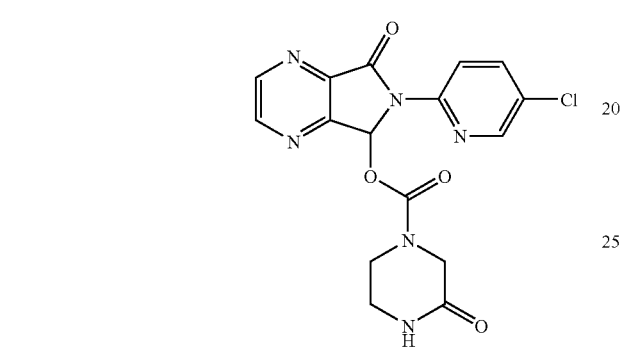

R = Aryl, alkyl, or vinyl

According to this method, carbonic acid 6-(5-chloro-pyridin-2-yl)-7-oxo-6,7-dihydro-5H-pyrrolo[3,4-b]pyrazin-5-yl ester alkyl ester, a material typically used to prepare zopiclone, is reacted with alkyl substituted or unsubstituted Piperazin-2-one. Enantiomerically pure forms of AmDMZ and MAmDMZ can be obtained by standard techniques such as, but not limited to, chiral chromatography.

Another method of preparing AmDMZ and MAmDMZ is illustrated below in Schemes IX and X:

Scheme IX

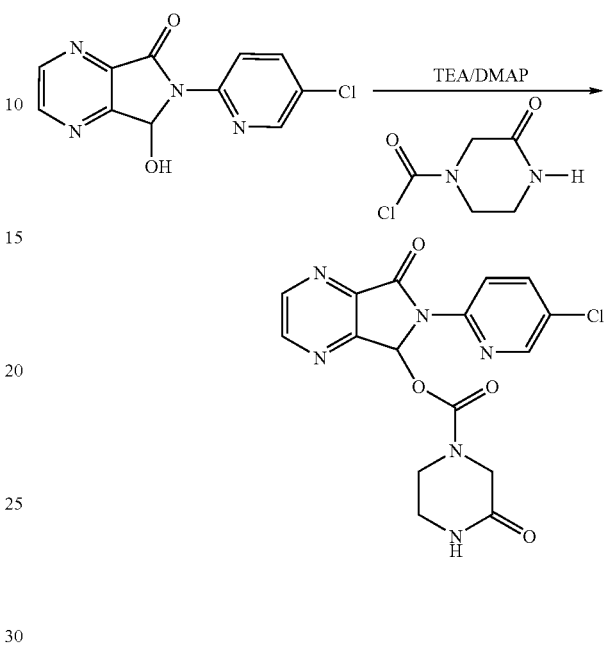

Scheme X

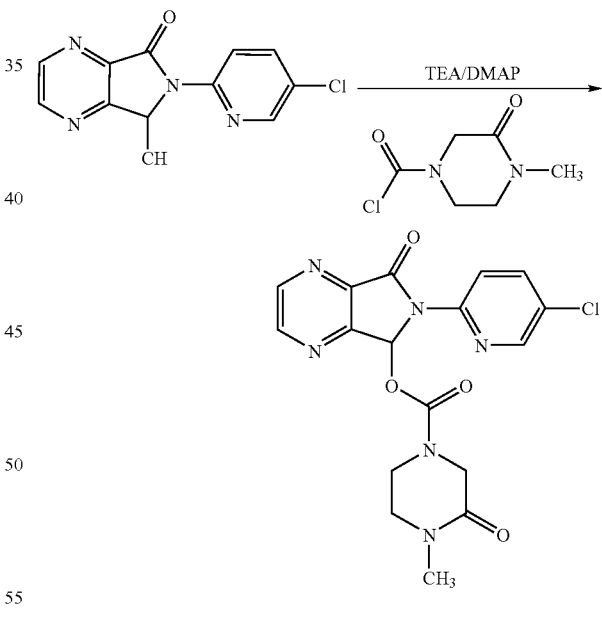

In this approach, 6-(5-Chloro-pyridin-2-yl)-7-hydroxy-6,7-dihydro-pyrrolo[3,4-b]pyrazin-5-one is reacted with triethylamine and 4-dimethylaminopyridine with an appropriate acid chloride to yield the desired product. Enantiomerically pure AmDMZ and MAmDMZ can be isolated using known techniques, such as chiral chromatography.

Yet another method of preparing compounds such as AmDMZ and MAmDMZ is illustrated below in Schemes XI and XII:

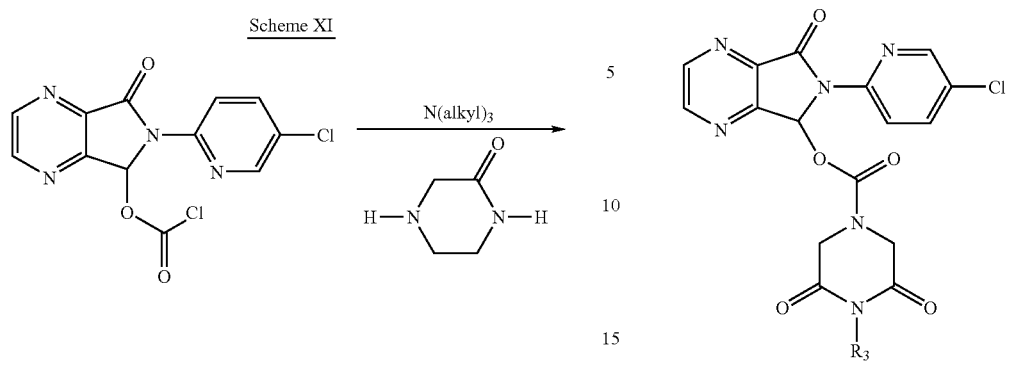

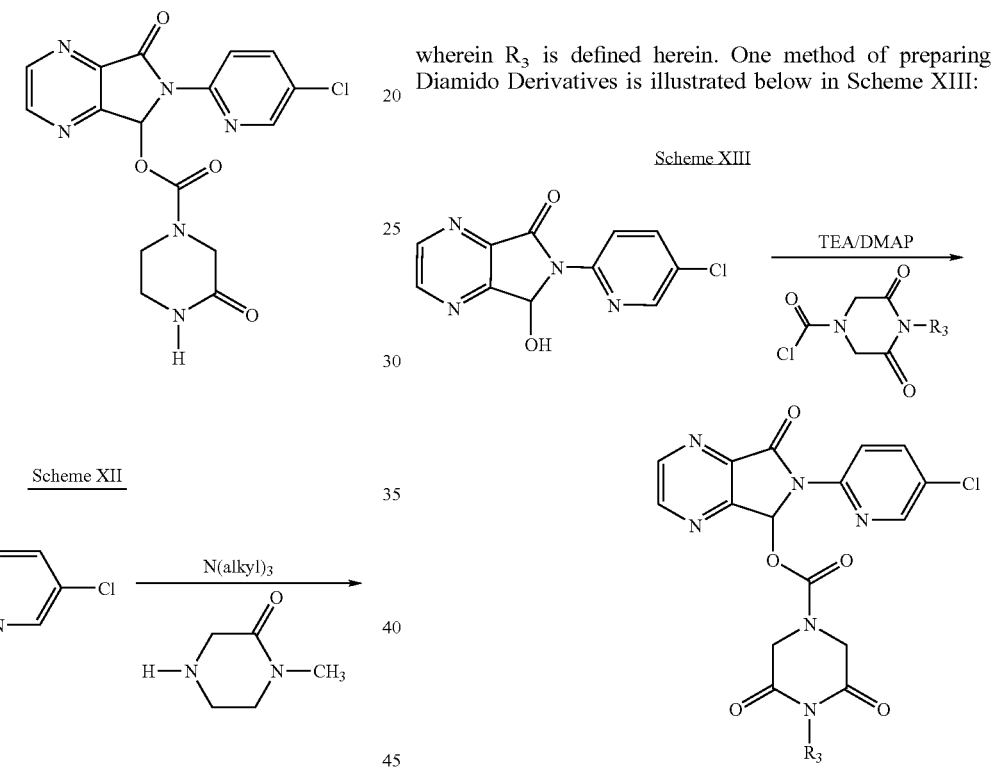

wherein $R_3$ is defined herein. One method of preparing Diamido Derivatives is illustrated below in Scheme XIII:

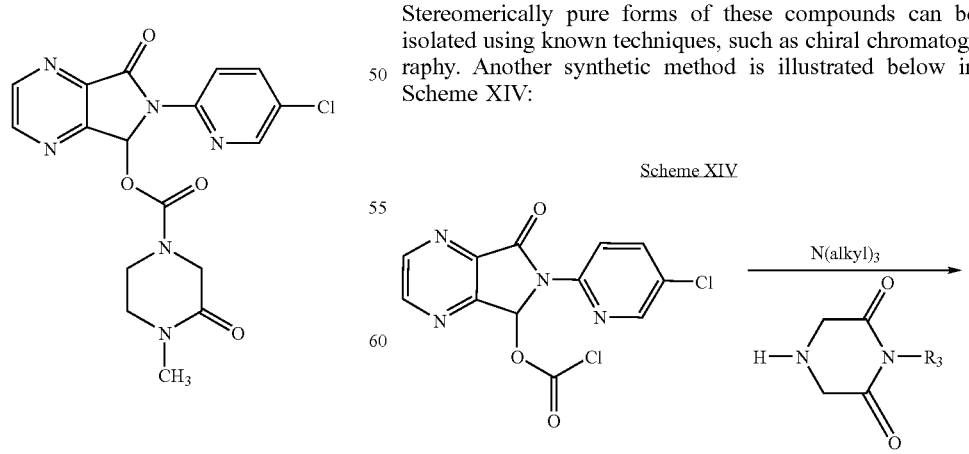

Stereomerically pure forms of these compounds can be isolated using known techniques, such as chiral chromatography. Another synthetic method is illustrated below in Scheme XIV:

Some of the compounds of the invention are collectively referred to herein as "Diamido Derivatives," and have the following structure:

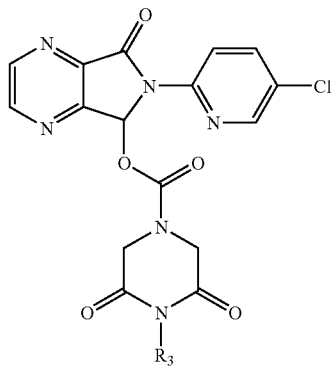

was obtained by column chromatography over silica gel (100% EtOAc as eluent) which gave the title compound (0.59 g, 62%) as a white solid. $^1$H NMR (400 MHz, CDCl$_3$) δ 2.98 (s, 3H), 3.35 (s, 2H), 3.71 (t, J=5.5 Hz, 2H), 4.14 (s, 2H), 5.13 (s, 2H), 7.35 (m, 5H).

1-Methyl-piperazin-2-one: To a magnetically stirred solution of 4-Methyl-3-oxo-piperazine-1-carboxylic acid tert-butyl ester (2.0 g, 8.06 mmol) in methanol (20 mL) under Ar atmosphere, 10% Pd/C was added. A hydrogen balloon was equipped to the reaction and the reaction mixture was stirred under a hydrogen atmosphere overnight at room temperature. The reaction mixture was filtered over celite in vacuo, and the mother liquors were concentrated in vacuo to provide the title compound (0.83 g, 90%) as a white solid.

$^1$H NMR (400 MHz, CDCl$_3$) δ 1.98 (bs, 1H), 2.90 (s, 3H), 3.01 (t, J=10.6 Hz, 2H), 3.25 (t, J=10.6 Hz, 2H), 3.43 (s, 2H).

5.2.1.2 Synthesis of Methylamidodesmethylzopiclone

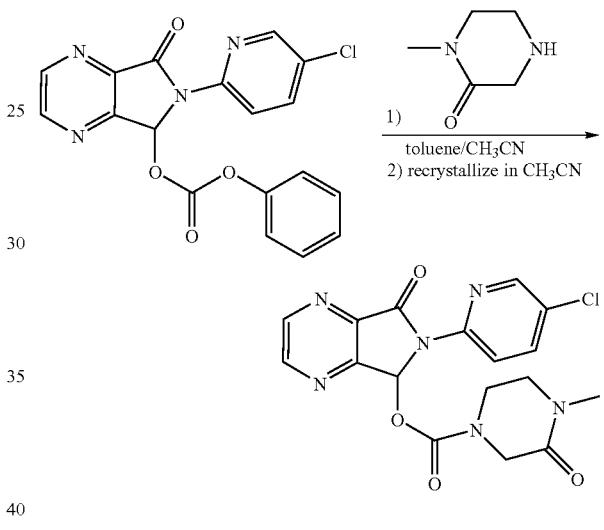

5.2 Alternative Methods of Synthesis
5.2.1 Methylamidodesmethylzopiclone
5.2.1.1 Synthesis of 1-Methyl-piperazine-2-one

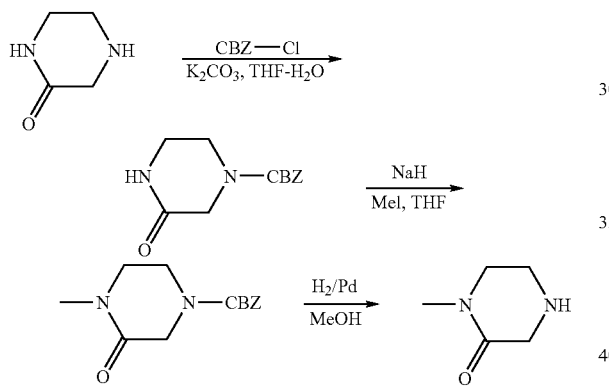

3-Oxo-piperazine-1-carboxylic acid benzyl ester: To a magnetically stirred solution of piperazin-2-one (2.0 g, 20.0 mmol) in THF (10 mL) at room temperature under Ar atmosphere, K$_2$CO$_3$ (8.25 g, 120 mmol), water (10 mL), and benzyl chloroformate (3.14 mL, 22.0 mmol) were added. The reaction mixture was stirred for 18 hours at room temperature. Water (50 mL) was added, and the aqueous phase was extracted with EtOAc (2×100 mL). The combined organic layers were washed with water, dried with MgSO$_4$, and concentrated in vacuo to the give the title compound (6.84 g, 100%). $^1$H NMR (400 MHz, CDCl$_3$) δ 3.37 (bs, 2H), 3.68 (t, J=4.7 Hz, 2H), 4.13 (s, 2H), 5.14 (s, 2H), 7.34 (m, 5H).

4-Methyl-3-oxo-piperazine-1-carboxylic acid tert-butyl ester: To a magnetically stirred solution of sodium hydride (0.75 g, 18.75 mmol) in THF (21 mL) at 0° C. under Ar atmosphere, 18-crown-6 (0.051 g, 0.193 mmol) and 3-oxo-piperazine-1-carboxylic acid benzyl ester (3.0 g, 4.27 mmol) were added. Methyl iodide (1.26 mL, 18.7 mmol) was added at 0° C. The reaction mixture was stirred for 2 hours at 0° C. Water (50 mL) was added, and the aqueous phase was extracted with EtOAc (2×100 mL). The combined organic layers were washed with water, dried with MgSO$_4$, and concentrated in vacuo to the crude product. The pure product To a magnetically stirred solution of lactamol phenyl carbonate (0.373 g, 0.978 mmol) in toluene (1.25 mL) and acetonitrile (5.0 mL) under Ar atmosphere at room temperature, 1-methyl-piperazine-2-one (0.30 g, 2.63 mmol) was added. The reaction mixture was stirred for 5 hours at 60° C. After cooling to room temperature, the reaction mixture was concentrated in vacuo. The crude residue was dissolved in warm acetonitrile (5 mL) and filtered to provide the title compound (0.11 g, 28%) as a white solid. $^1$H NMR (400 MHz, CDCl$_3$) δ 2.95 (s, 3H), 3.10 (m, 1H), 3.40 (m, 1H), 3.48 (m, 1H), 3.81 (m, 2H), 4.20 (m, 1H), 7.78 (d, J=1.4 Hz, 1H), 8.00 (s, 1H), 8.31 (m, 1H), 8.51 (d, J=8.4 Hz, 1H), 8.84 (s, 1H), 8.90 (s, 1H). $^{13}$C NMR (75 MHz, CDCl$_3$) δ 34.7, 41.0, 47.6, 48.1, 79.4, 116.4, 128.7, 138.5, 146.8, 148.2, 148.6. Mass spectrum m/e 403 (M$^+$).

5.2.2 Morpholine-4-carboxylic acid 6-(5-chloro-pyridin-2-yl)-7-oxo-6,7-dihydro-5H-pyrrolo[3,4-β]pyrazin-5-yl ester Morpholine-4-carboxylic acid 6-(5-chloro-pyridin-2-yl)-7-oxo-6,7-dihydro-5H-pyrrolo[3,4-β]pyrazin-5-yl ester was prepared from 4-methyl-3-oxo-piperazine-1-carboxylic acid tert-butyl ester and morpholine using a similar procedure described in Section 5.2.1, above. $^1$H NMR (400 MHz, CDCl$_3$) δ 3.08–3.54 (m, 8H), 7.77 (s, 1H), 8.08 (dd, J=2.6, 8.8 Hz, 1H), 8.37 (d, J=8.8 Hz, 1H), 8.55 (d, J=2.5 Hz, 1H), 8.93 (d, J=2.5 Hz, 1H), 8.97 (d, J=2.5 Hz, 1H).

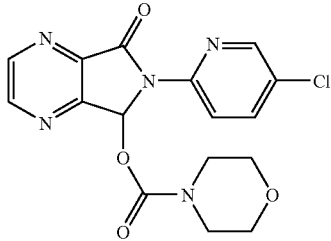

5.2.3 Ureadesmethylzopiclone

Ureadesmethylzopiclone was prepared from 4-methyl-3-oxo-piperazine-1-carboxylic acid tert-butyl ester and piperazine-1-carboxylic acid amide using a similar procedure described in Section 5.2.1, above. $^1$H NMR (400 MHz, CDCl$_3$) δ 3.09–3.42 (m, 8H), 6.01 (s, 2H), 7.77 (s, 1H), 8.08 (dd, J=2.6, 8.8 Hz, 1H), 8.38 (d, J=8.8 Hz, 1H), 8.53 (d, J=2.5 Hz, 1H), 8.93 (d, J=2.5 Hz, 1H), 8.97 (d, J=2.5 Hz, 1H).

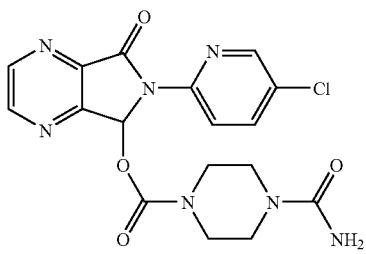

5.2.4 Carboethoxydesmethylzopiclone

Carboethoxydesmethylzopiclone was prepared from 4-methyl-3-oxo-piperazine-1-carboxylic acid tert-butyl ester and piperazine-1-carboxylic acid ethyl ester using a similar procedure described in Section 5.2.1, above. $^1$H NMR (400 MHz, CDCl$_3$) δ 1.22 (t, J=7.0 Hz, 3H), 3.27 (m, 4H), 3.49 (m, 4H), 4.11 (q, J=7.3 Hz, 2H), 7.78 (dd, J=2.2, 8.8 Hz, 1H), 8.00 (s, 1H), 8.35 (d, J=2.2 Hz, 1H), 8.51 (d, J=8.8 Hz, 1H), 8.84 (d, J=2.5 Hz, 1H), 8.88(d, J=2.5 Hz, 1H).

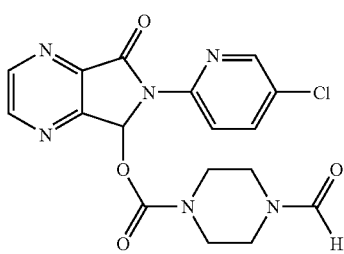

5.2.5 Formyldesmethylzopiclone

Formyldesmethylzopiclone was prepared from 4-methyl-3-oxo-piperazine-1-carboxylic acid tert-butyl ester and piperazine-1-carbaldehyde using a similar procedure described in Section 5.2.1, above. $^1$H NMR (400 MHz, CDCl$_3$) δ 3.10–3.64 (m, 8H), 7.25 (s, 1H), 7.80 (dd, J=2.5 Hz, 8.8 Hz, 1H), 8.02 (s, 1H), 8.35 (d, J=1.8 Hz, 1H), 8.53 (d, j=8.8 Hz, 1H), 8.84 (d, J=2.5 Hz, 1H), 8.90 (d, J=2.5 Hz, 1H).

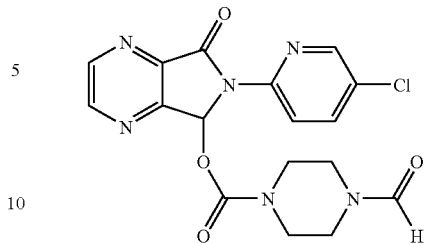

5.3 Determination of Biological Activity

A pharmacologic study is conducted to determine the relative potency, comparative efficacy, and binding affinity of zopiclone derivatives. The pharmacologic profile of hypnotic-sedative, anxiolytic agents of the benzodiazepine class is well established, and has been extended to non-benzodiazepine agents of the cyclopyrrolone class. See, e.g., *Goodman & Gilman's The Pharmacological Basis of Therapeutics*, Hardman, J. G., et al., eds. ch. 17, pp. 361–396 (9th ed., 1996); Bardone, M. C., et al., Abstract No. 2319, 7th *Int. Congr. Pharm. Paris*, (July, 1978: Pergamon Press, London); Julou, L. et al., *Pharmacology, Biochemistry and Behavior*, 23:653–659 (1985).

A variety of experimental models can be used to characterize the various activities of zopiclone derivatives, including their anticonvulsant, myorelaxant, anti-aggressive, sedative-hypnotic, and anxiolytic (i.e., anti-anxiety) activities. In an examination of each element of the pharmacologic profile, zopiclone derivatives are compared with pharmacologic standards such as nitrazepam and diazepam in a variety of animal models. The dose (mg/kg) of each agent that is capable of inhibiting by 50% (the ID$_{50}$ or ED$_{50}$) of an induced response in rodents, for example, provides the basis for comparison. Pentylenetetrazole-induced, picrotoxin convulsions, and electrically-induced convulsions can thus be used to demonstrate the anti-convulsant activity of zopiclone derivatives. Haefely, W., *Psychotropic Agents*, Hofmeister, F. and Stille, G., eds., part 11, pp. 12–262 (Springer Verlag, Berlin: 1981). Further, in the rat, in the amygdala kindled model of epilepsy, daily electrical stimulation of the amygdala induces a progressive increase of epileptic afterdischarge duration, with increasing epileptic behavioral symptoms, producing in about two weeks a generalized convulsive crisis. Presumably, previously ineffective stimuli have sensitized neuronal pathways, and it has been suggested that a similar mechanism may exist for the induction of an anxiety state in man after repeated stresses.

Similar models are available for determination of the myorelaxant, anti-aggressive, and sedative-hypnotic activities of zopiclone derivatives in both mice and rats. See, Julou, L. et al., *Pharmacology, Biochemistry and Behavior*, 23:653–659 (1985).

The pharmacologic activity of zopiclone derivatives may also be compared with benzodiazepines for their affinity for binding to both CNS and peripheral benzodiazepine receptors. In this biochemical affinity binding study, the binding of $^3$H-radiolabeledzopiclone derivatives is studied in a synaptosomal membrane preparation of cerebral tissue from female rat brain. The tissue is preferably prepared by homogenization in ice-cold isosmotic (0.32 M) sucrose, and centrifugation, first at low speed (1,000×g for 10 minutes), with the resultant supernatant solution then being centrifuged at high speed (48,000×g for 20 minutes). The resulting pellet is suspended in Kreb-Tris buffer at pH 7.4, and the concentration of protein is adjusted to 15 mg/ml. This synaptosomal membrane preparation may be stored at −18° C. until used at room temperature (e.g., about 22° C.) with the radio-cyclopyrrolone in Kreb-Tris buffer solution pH 7.4. Following a 30-minute incubation, separation of the bound and free drug is performed by centrifugation at 1,000×g for 10 minutes in scintillation vials. The supernatant solution is collected, the pellet is dissolved in a counting vehicle, and the radioactivity is counted using a liquid scintillation counter. The original supernatant solution from the first incubation, which contains unbound radiolabeled drug, may be used in additional binding studies using the same method. Additional controls involve, for instance, study of the radioactivity bound in the presence of 10 μM flunitrazepam (a benzodiazepine), which experiment is useful in assessing non-specific binding. Furthermore, the binding of various concentrations of radiolabeledzopiclone derivatives in the presence of a fixed concentration of GABA provides additional information as to the modulation of the GABA-ergic system byzopiclone derivatives. See, Jacqmin, P., et al., *Arch. Int. Pharmacodyn,* 282:26–32 (1986); Jacqmin, P., et al., *J. Pharm. Belg.* 40:35–54 (1985). With regard to peripheral benzodiazepine receptors and their distinction from central benzodiazepine binding sites, see, e.g., Verma, A. and Snyder, S. H., *Ann. Rev. Pharmacol. Toxicol.* 29:307–322 (1989), which is hereby incorporated by reference.

5.4 Tablet Dosage Forms

Suitable ingredients of a tablet dosage form of a zopiclone derivative are provided in Table 1.

TABLE 1

| Component | Quantity per Tablet (mg) |
|---|---|
| zopiclone derivative | 75 |
| Lactose | 125 |
| Corn Starch | 5.0 |
| Water (per thousand tablets) | 30.0 ml* |
| Magnesium Stearate | 0.5 |

*The water evaporates during manufacture.

The active ingredient is blended with the lactose until a uniform blend is formed. The smaller quantity of corn starch is blended with a suitable quantity of water to form a corn starch paste. This is then mixed with the uniform blend until a uniform wet mass is formed. The remaining corn starch is added to the resulting wet mass and mixed until uniform granules are obtained. The granules are then screened through a suitable milling machine, using a ¼ inch stainless steel screen. The milled granules are then dried in a suitable drying oven until the desired moisture content is obtained. The dried granules are then milled through a suitable milling machine using ¼ mesh stainless steel screen. The magnesium stearate is then blended and the resulting mixture is compressed into tablets of desired shape, thickness, hardness and disintegration. Tablets may be coated by standard aqueous or nonaqueous techniques.

Another tablet dosage formulation suitable for use with an active ingredient of the invention is provided by Table 2:

TABLE 2

| | Quantity per Tablet (mg) | | |
|---|---|---|---|
| Component | Formula A | Formula B | Formula C |
| zopiclone derivative | 20 | 40 | 100 |
| Lactose BP | 134.5 | 114.5 | 309.0 |
| Starch BP | 30 | 30 | 60 |

TABLE 2-continued

| | Quantity per Tablet (mg) | | |
|---|---|---|---|
| Component | Formula A | Formula B | Formula C |
| Pregelatinized Maize Starch BP | 15 | 15 | 30 |
| Magnesium Stearate | 0.5 | 0.5 | 1.0 |
| Compression Weight | 200 | 200 | 500 |

The active ingredient is sieved and blended with lactose, starch, and pregelatinized maize starch. Suitable volumes of purified water are added and the powders are granulated. After drying, the granules are screened and blended with the magnesium stearate. The granules are then compressed into tablets using punches.

Compressed tablet formulations of zopiclone derivatives may be made using the ingredients provided in Table 3:

TABLE 3

| | Compressed Tablet Formulations | | |
|---|---|---|---|
| Component | 0.1 mg tablet (amount in mg) | 5 mg tablet (amount in mg) | 20 mg tablet (amount in mg) |
| zopiclone derivative | 0.1 | 5.0 | 20.0 |
| Microcrystalline Cellulose | 90.0 | 90.0 | 90.0 |
| Pregelatinized Starch | 102.7 | 97.8 | 82.8 |
| Croscarmellose | 7.0 | 7.0 | 7.0 |
| Magnesium Stearate | 0.2 | 0.2 | 0.2 |

The active ingredient is sieved through a suitable sieve and blended with the non-lactose excipients until a uniform blend is formed. The dry blend is screened and blended with the magnesium stearate. The resulting powder blend is then compressed into tablets of desired shape and size. Tablets of other strengths may be prepared by altering the ratio of the active ingredient to the excipient(s) or modifying the tablet weight.

Tablets of other strengths may be prepared by altering the ratio of active ingredient to pharmaceutically acceptable carrier, the compression weight, or by using different punches.

5.5 Capsule Dosage Forms

Capsules of zopiclone derivatives may be made using the ingredients provided in Table 4:

TABLE 4

| | Capsule Unit Dosage Forms | | |
|---|---|---|---|
| | Quantity per Capsule (mg) | | |
| Formulation | A | B | C |
| zopiclone derivative | 50.0 | 100.0 | 200.0 |
| Lactose | 48.5 | 148.5 | 48.5 |
| Titanium Dioxide | 0.5 | 0.5 | 0.5 |
| Magnesium Stearate | 1.0 | 1.0 | 1.0 |
| Fill Weight | 100.0 | 250.0 | 250.0 |

The active ingredient is sieved and blended with the excipients. The mixture is filled into suitably sized two-piece hard gelatin capsules using suitable machinery. Other doses may be prepared by altering the ratio of the active ingredient and pharmaceutically acceptable carrier, the fill weight and, if necessary, by changing the capsule size to suit.

Hard gelatin capsules of zopiclone derivatives may be made using the ingredients provided in Table 5:

TABLE 5

Hard Gelatin Capsule Unit Dosage Forms

| Component | 0.1 mg capsule (amount in mg) | 5 mg capsule (amount in mg) | 20 mg capsule (amount in mg) |
|---|---|---|---|
| zopiclone derivative | 0.1 | 5.0 | 20.0 |
| Microcrystalline Cellulose | 90.0 | 90.0 | 90.0 |
| Pre-gelatinized Starch | 102.7 | 97.8 | 82.8 |
| Croscarmellose | 7.0 | 7.0 | 7.0 |
| Magnesium Stearate | 0.2 | 0.2 | 0.2 |

The active ingredient is sieved and blended with the excipients listed. The mixture is filled into suitably sized two-piece hard gelatin capsules using suitable machinery and methods well known in the art. See, e.g., Remington's Pharmaceutical Sciences, 16th or 18th Editions, each incorporated herein. Other doses may be prepared by altering the fill weight and, if necessary, changing the capsule size to suit. Any of the stable, non-lactose hard gelatin capsule formulations above may be formed.

The embodiments of the invention described above are intended to be merely exemplary, and those skilled in the art will recognize, or be able to ascertain using no more than routine experimentation, numerous equivalents to the specific procedures described herein. All such equivalents are considered to be within the scope of the invention and are encompassed by the following claims.

What is claimed is:

1. An enantiomerically pure compound of Formula 3:

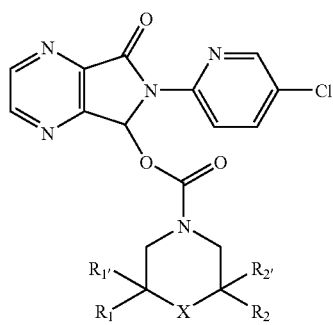

Formula 3 or a pharmaceutically acceptable salt, solvate, hydrate or prodrug thereof, wherein: X is O or $NR_3$; $R_1$ and $R_{1'}$ are both H or when taken together are =O; $R_2$ and $R_{2'}$ are both H or when taken together are =O; and $R_3$ is H, alkyl, aryl, arylalkyl or —$COR_4$, wherein $R_4$ is H, amine, alkyl, alkoxy, aryl, aryloxy, arylalkyl, or O-arylalkyl; provided that when X is $NR_3$ and $R_1$, $R_{1'}$, $R_2$, and $R_{2'}$ are all H, then $R_3$ is not H or methyl.

2. The compound of claim 1 wherein X is $NR_3$ and $R_1$ and $R_{1'}$ are both H.

3. The compound of claim 2 wherein $R_2$ and $R_{2'}$ are taken together to be =O.

4. The compound of claim 1 wherein X is $NR_3$ and $R_1$ and $R_{1'}$ are taken together to be =O and $R_2$ and $R_{2'}$ are taken together to be =O.

5. The compound of claim 1 wherein X is $NR_3$ and $R_1$, $R_{1'}$, $R_2$, and $R_{2'}$ are all H and $R_3$ is —$COR_4$, wherein $R_4$ is H, alkyl, $NH_2$, or alkoxyalkyl.

6. The compound of claim 5 wherein $R_4$ is H, $CH_3$, $NH_2$ or —$OCH_2CH_3$.

7. The compound of claim 1, wherein X is O and $R_1$, $R_{1'}$, $R_2$ and $R_{2'}$ are all H.

8. A compound selected from the following:

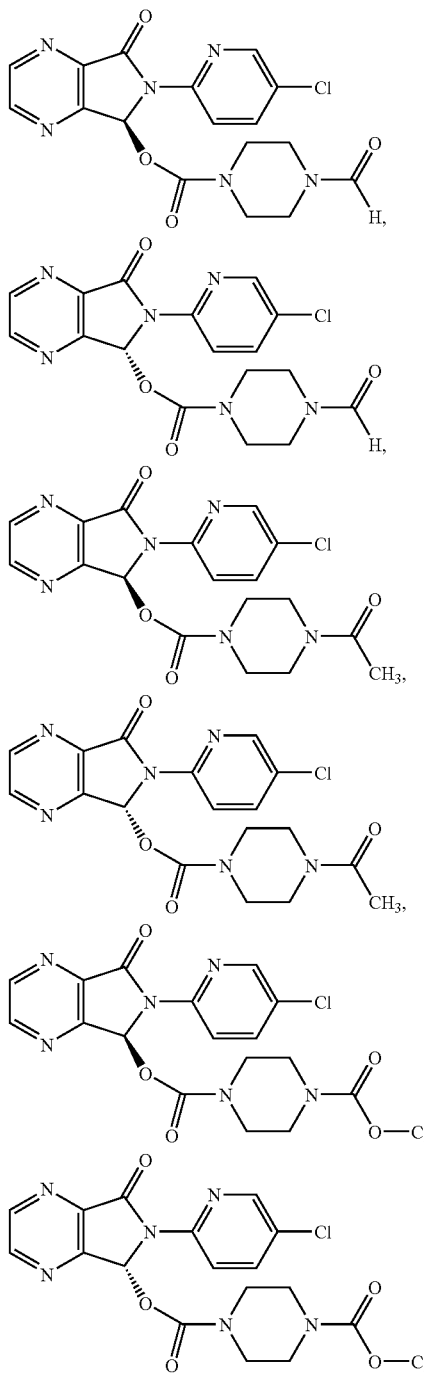

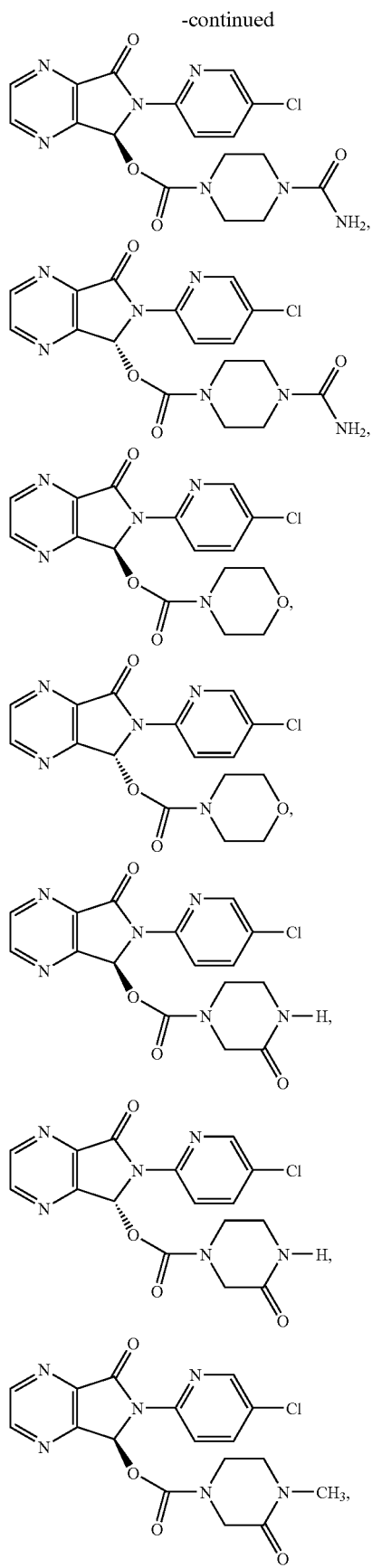
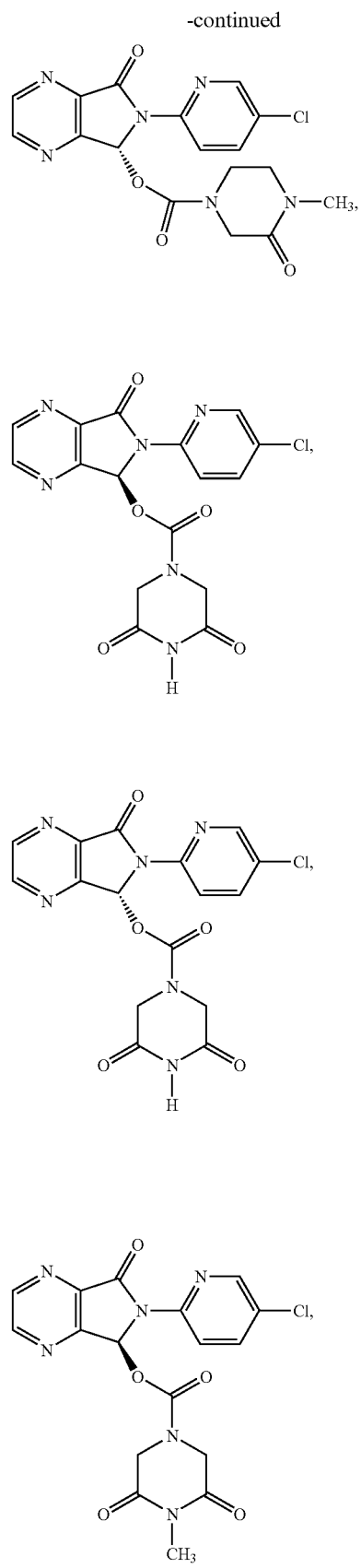

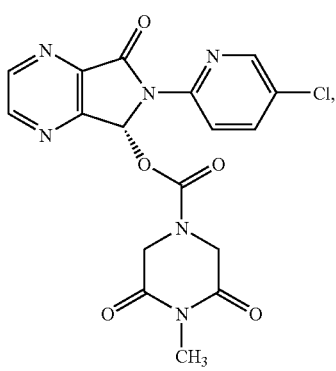

or a pharmaceutically acceptable salt, solvate, hydrate or prodrug thereof.

9. A pharmaceutical composition comprising a compound of Formula 3:

Formula 3

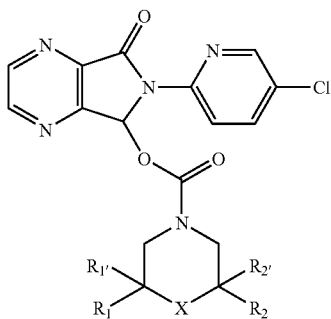

or a pharmaceutically acceptable salt, solvate, hydrate or prodrug thereof, wherein: X is O or $NR_3$; $R_1$ and $R_{1'}$ are both H or when taken together are =O; $R_2$ and $R_{2'}$ are both H or when taken together are =O; and $R_3$ is H, alkyl, aryl, arylalkyl or —$COR_4$, wherein $R_4$ is H, amine, alkyl, alkoxy, aryl, aryloxy, arylalkyl, or O-arylalkyl; provided that when X is $NR_3$ and $R_1$, $R_{1'}$, $R_2$, and $R_{2'}$ are all H, then $R_3$ is not H or methyl; and a pharmaceutically acceptable excipient.

10. The pharmaceutical composition of claim 9 wherein X is $NR_3$ and $R_1$ and $R_{1'}$ are both H.

11. The pharmaceutical composition of claim 10 wherein $R_2$ and $R_{2'}$ are taken together to be =O.

12. The pharmaceutical composition of claim 9 wherein X is $NR_3$ and $R_1$ and $R_{1'}$ are taken together to be =O and $R_2$ and $R_{2'}$ are taken together to be =O.

13. The pharmaceutical composition of claim 9 wherein X is $NR_3$ and $R_1$, $R_{1'}$, $R_2$, and $R_{2'}$ are all H and $R_3$ is —$COR_4$, wherein $R_4$ is H, alkyl, $NH_2$ or alkoxyalkyl.

14. The pharmaceutical composition of claim 13 wherein $R_4$ is H, $CH_3$, $NH_2$ or —$OCH_2CH_3$.

15. The pharmaceutical composition of claim 9 wherein X is O and $R_1$, $R_{1'}$, $R_2$ and $R_{2'}$ are all H.

16. The pharmaceutical composition of claim 9 wherein the compound of Formula 3 is stereomerically pure.

* * * * *

UNITED STATES PATENT AND TRADEMARK OFFICE
CERTIFICATE OF CORRECTION

| | |
|---|---|
| PATENT NO. | : 7,189,715 B2 |
| APPLICATION NO. | : 10/691628 |
| DATED | : March 13, 2007 |
| INVENTOR(S) | : Jerussi et al. |

It is certified that error appears in the above-identified patent and that said Letters Patent is hereby corrected as shown below:

Title Page, left column, in "Notice," please revise as follows:

-- Subject to any disclaimer, the term of this patent is extended or adjusted under 35 U.S.C. 154(b) by ~~320~~ 420 days. --

Signed and Sealed this

Eighth Day of July, 2008

JON W. DUDAS
*Director of the United States Patent and Trademark Office*